United States Patent [19]

Qian et al.

[11] Patent Number: 5,658,963
[45] Date of Patent: Aug. 19, 1997

[54] ONE-COMPONENT PRIMER/BONDING-RESIN SYSTEMS

[75] Inventors: Xuejun Qian, Bartlett; Byoung I. Suh, Oak Brook; Martin Hamer, Skokie; Russell H. Tobias, Cary, all of Ill.

[73] Assignee: Bisco, Inc., Itasca, Ill.

[21] Appl. No.: 382,617

[22] Filed: Feb. 2, 1995

[51] Int. Cl.$^6$ .................................................. C08F 2/46
[52] U.S. Cl. .................... 522/14; 522/908; 106/35; 523/116; 433/228.1
[58] Field of Search .................. 522/14, 908; 106/35; 523/116; 433/228.1

[56] References Cited

U.S. PATENT DOCUMENTS

| | | | |
|---|---|---|---|
| 4,514,527 | 4/1985 | Bowen | 523/115 |
| 4,525,256 | 6/1985 | Martin | 204/159.18 |
| 4,544,467 | 10/1985 | Bunker et al. | 204/159.24 |
| 4,551,550 | 11/1985 | Bey | 564/215 |
| 4,588,756 | 5/1986 | Bowen | 523/116 |
| 4,645,456 | 2/1987 | James | 433/217.1 |
| 4,657,941 | 4/1987 | Blackwell et al. | 522/14 |
| 4,659,751 | 4/1987 | Bowen | 523/116 |
| 4,816,495 | 3/1989 | Blackwell et al. | 522/14 |
| 4,966,934 | 10/1990 | Huang et al. | 524/315 |
| 5,270,351 | 12/1993 | Bowen | 523/116 |
| 5,276,068 | 1/1994 | Waknine | 522/28 |
| 5,295,824 | 3/1994 | Wong | 433/9 |
| 5,304,558 | 4/1994 | Kaneko et al. | 514/253 |
| 5,304,585 | 4/1994 | Bunker | 523/116 |
| 5,320,886 | 6/1994 | Bowen | 428/34.1 |
| 5,334,625 | 8/1994 | Ibsen et al. | 523/115 |
| 5,348,988 | 9/1994 | Suh et al. | 523/118 |

FOREIGN PATENT DOCUMENTS

WO93/02630  2/1993  WIPO.

OTHER PUBLICATIONS

Suh, Byoung I., *Journal of Esthetic Dentistry*, 3(4):139–147 (Jul./Aug. 1991).

*Primary Examiner*—Mark Chapman
*Attorney, Agent, or Firm*—Marshall, O'Toole, Gerstein, Murray & Borun

[57] ABSTRACT

Primer/bonding-resin compositions include certain hydrophilic monomers, reactive diluent monomers, high viscosity adhesive resins and photo-initiator systems, all provided in a one-component solution containing ethanol or acetone or other suitable solvents. Methods of use of such compositions include a single step application for priming and imparting enhanced adhesion between dental substrates and dental restoratives or components.

40 Claims, No Drawings

5,658,963

ONE-COMPONENT PRIMER/BONDING-RESIN SYSTEMS

BACKGROUND OF THE INVENTION

1. Field of the Invention

The present invention relates generally to adhesive and primer bonding systems. More specifically, the present invention relates to combined primer/bonding-resin compositions which are light-curable and shelf-stable, and to simplified bonding systems using such compositions. The compositions and methods of the present invention enhance the bonding of composite resins, metals and other dental prostheses to tooth tissue and to other substrates.

2. Description of Related Technology

Recent advances in dental restorative techniques include the use of materials such as composite resins to effect tooth filling and restoration instead of metal amalgams. Other advances include the use of new dental components such as thin wire braces and other types of dental components made of metal, ceramics, resins or other bio-compatible substances. Depending on the clinical picture, such restoratives and components may need to be applied directly to the tooth dentin and/or enamel, or may need to be applied to other bio-compatible substrates such as metals, ceramics, resins or amalgams which may already exist in the patient and/or are to be added as part of the clinical treatment.

Common to the foregoing techniques, and many older forms of dental restorative techniques, is the general need for bonding systems for effecting and enhancing the bonding of the restorative or other dental component to the chosen dental substrate. Ideal/y, such enhancement would provide bond strengths which approach the strength of the underlying substrates. In addition, ideal bonding systems would also be simple for the dental professional to use in a manner which requires a minimum of time for the patient in the chair.

Several bonding systems have been reported in the literature which have achieved some, but not all of the above-stated goals. Such older bonding systems can be divided into two general categories, multiple-component primer systems and single-component primer systems.

A general discussion of multiple-component bonding systems and their predecessors is set out in Suh, "All-Bond—Fourth Generation Dentin Bonding System," *J. Esthetic Dentistry*, Vol. 3, No. 4, pp. 139–147 (July-August, 1991) and in Bowen U.S. Pat. No. 5,270,351 at Col. 1, lines 29-Col. 2, line 36 and Col. 2, lines 54–64, the disclosures of which are hereby incorporated by reference. Briefly summarized, the early generation bonding systems generally disclosed at Col. 1 and 2 of the '351 patent began with simple pretreatment of the dental substrate with mordants and/or acidic solutions before application of the dental restorative or component. Such systems, while simple to use, did not provide very high bond strengths on substrates such as tooth dentin.

Those low bond strengths led to the development of the multiple-component bonding systems discussed at Col. 2 of the '351 patent and discussed in detail in the *J. Esthetic Dentistry* article at pp. 139–147. Such systems generally employed the older generation system's first step of pretreatment of tooth dentin or enamel with acidic solutions to decalcify and remove dentin smear layer and to etch tooth enamel. The multi-component systems then employed two or more separate "primer" or "adhesive enhancing" compounds to further enhance bonding between the substrate and the dental restorative. However, the primers in such systems must either (1) be applied separately and sequentially to the dental substrate, or (2) must be mixed together by the dental professional in the office immediately before use on the patient to prevent premature polymerization of the components.

The first type of such multiple-component primer systems is exemplified in Bowen U.S. Pat. Nos. 4,514,527, 4,551,550, 4,558,756 and 4,659,751 discussed at Col. 2 of the '351 patent. Those earlier patents disclose, inter alia, two or three component primer systems employing the separate steps of treating the dental substrate with (1) an acidic acid solution of inorganic acids, polycarboxylic acids and metal salts of such acids capable of changing valence states, (2) applying a first primer compound comprising N-arylglycine derivatives to the substrate, followed by (3) applying a second adhesive bonding monomer to the substrate. Although some of those systems report achieving moderate bond strengths for bonding to substrates such as tooth dentin, from about 1600 to about 2500 p.s.i (11–17 Mega Pascals (1 MPa=145 p.s.i.)), such multi-component/multi-step methods are necessarily complicated for the dental professional and time-consuming for the patient.

More recently, Bowen and others, including applicant's assignee, Bisco, Inc., have reported development of two-component primer systems. See e.g., Bowen U.S. Pat. Nos. 5,320,886 and 5,270,351, Suh et al. article cited above and U.S. Pat. No. 5,348,988 and Bunker U.S. Pat. No. 4,544,467. Such systems involve inter alga steps whereby the dental professional admixes the two primer components immediately prior to application of the mixture to the dental substrate. Immediate application is required in such systems because the primer composition begins to polymerize upon mixing due to the chemical nature of the primer molecules, at least one of which contains ethylenically unsaturated (vinyl) groups whose polymerization is initiated by the tertiary amine group present on the other primer component of the system.

A different type of a two-component primer bonding system is disclosed in Waknine U.S. Pat. No. 5,276,068. That two-component system comprises a polymerization initiator and a polymerizable compound which are packaged separately. The first step in that system requires application of polymerization initiator alone to the dental substrate. In a second step, the polymerizable compound is applied to the substrate. Polymerization begins when the polymerizable compound comes into contact with the initiator on the substrate surface.

Most of the aforesaid multiple-component primer systems were reported as providing only moderate dentin adhesive bonding strengths. For example, the data included in the Bowen '351 and '886 patents show dentin adhesive bond strengths of from about 10 to about 15 MPa. Moreover, the higher bond strengths reported in the '351 patent were achieved only after an additional step and component, comprising applying an unfilled adhesive resin monomer to the primed substrate before application of the dental restorative composite material, was added to the restorative process. (See '351 patent, Example 1.) The Waknine '068 patent also reports relatively low bond strengths in the 10 MPa range and also used an additional step of application of a commercial bonding resin (see Examples 22–23.) Bunker et al. reported slightly lower dentin shear bond strengths of between about 5 MPa and 8 MPa (49.3 to 86.5 kg/cm$^2$).

Surprisingly, Suh et al.'s two-component primer system achieved bond strengths of between 22 and 27 MPa for dentin bonding, which approaches or equals the point of cohesive failure of tooth dentin. High bond strengths of around 23-26 MPa were also achieved with that two component priming system for bonding to tooth enamel. (See, e.g., J. Esthetic Dentistry article, FIGS. 5 and 12.) In addition, the assignee's two-component primer system permits either light-cure or self-cure of the applied primers, adding versatility to the treatment protocol for the dental professional.

Although applicants assignee has achieved near ideal bond strengths with its aforementioned two-component primer system, that system, and the other two-component systems identified above, necessarily requires the dental professional to perform the admixing of primers and/or primers and initiator while the patient waits in the chair, complicating the overall restorative process and increasing the treatment time. Moreover such systems generally require the use of an additional component, an unfilled bonding resin, applied as an additional step in the process in order to achieve such high bond strengths, further complicating the restorative process.

Recently there have been reported certain "one-component" dental bonding systems. See, for example, Blackwell et at. U.S. Pat. Nos. 4,657,941 and 4,816,495 and Huang et at. U.S. Pat. No. 4,966,934 all of which are assigned to Dentsply Research and Development Corporation (hereinafter also collectively referred to as the Dentsply patents) and Bunker U.S. Pat. No. 5,304,585.

The Bunker et al. system is reported as involving polymerizable phosphorous acid ester adhesives. Such compositions are generally disclosed therein as capable of being packaged with polymerization initiators in the presence of polymerization inhibitors and other compounds in one package. (See '585 patent, col. 10, line 31 to col. 11, line 8.) However, such one-component packaging is not exemplified in the '585 patent. Instead, a two-component was tested in Example 1 of that patent, involving admixing of the polymerization initiator sodium benzenesulfinate first component with the phosphorous ester monomer second component immediately before application to the tooth substrate. Bunker et al. also reported relatively low bond strength to dentin of around 9 MPa. (See '585 patent, col. 12, lines 16-42.)

The Dentsply patents also disclose alleged one-component dentin and enamel bonding primer and adhesive systems. Such systems are reported as based inter alia on phosphorous-containing adhesion promoter compounds. However, the phosphorous-based bonding systems disclosed in the examples of '941 and '495 patents all gave relatively low bond strengths of 8.39 MPa or less.

The dipentaerythritol pentaacrylate phosphoric acid ester-based (PENTA) bonding systems disclosed in the '934 patent were reported as generating higher dentin bond strengths in the range of 10-27 MPa. (See '934 patent Example 10.) However, also reported therein is data showing that the higher reported bond strength systems were not stable over time, with the 27 MPa strength system reported as decreasing to around 10 MPa or less after 1-2 weeks storage of the system at elevated temperatures. (See '934 patent, Table VIII.) Moreover, the higher bond strengths reported in the '934 patent were in actuality two-component systems in which a second commercial, unfilled adhesive bonding resin component was used after application of the phosphorous primer composition. (See Example 4 and Example 10 at Col. 17, line 60-Col. 18, line 53 and Tables IX and X.) The "most promising" PENTA-based bonding systems disclosed in the '934 patent were further tested with that additional second adhesive component and step which were reported to provide bonding strengths from about 17 to 20 MPa. (See Table X.) In all three Dentsply patents, the primer curing system was reported as light-curing done after either application of the composite resin material and/or after application of a separate adhesive resin. (See Example 4 of '941,495 and 934 patents.)

U.S. Pat. No. 4,525,256 discloses certain one component photopolymerizable resins containing certain tertiary amine accelerators. However, such compositions are composite (filled) resins, and not dental primer or adhesive compositions. (See '256 patent, Examples 1-3.)

U.S. Pat. No. 5,295,824 discloses inter alia plastic orthodontic devices with a "shelf-stable" monomeric adhesive layer pre-coated and "solvated" into the plastic device. The bond strengths reported therein are about 10-20 kg, which if meant to be $kg/cm^2$, translate to rather low levels of around 2-4 Mpa.

PCT application publication No. WO/93/02630 discloses an adhesive-coated orthodontic bracket. The bracket's adhesive layer comprises ethoxylated diglycidyimethacrylate of Bisphenol A (Bis-GMA), Bis-GMA and/or other monomers and photo-initiator catalysts and inhibitors. The bond strength of such pre-coated brackets were reported to be in the range of 54-104 $kg/cm^2$ (about 5-10 Mpa).

There is, therefore, a need in the art for true one-component primer/bonding-resin systems which provide high bond strengths, exhibit good stability and permit simplification of the overall restorative process.

SUMMARY OF THE INVENTION

In accordance with the present invention, there are provided novel primer/bonding-resin compositions which comprise a combination of both a primer component and an adhesive resin component in a single composition. Such novel combined primer/bonding-resin compositions according to the present invention, explained in more detail below, promote adhesion between a dental substrate and dental restorative material or other dental devices. Primer/bonding-resin compositions according to the invention comprise certain hydrophilic monomers, reactive diluent monomers, high viscosity adhesive resins and photo-initiator systems, all provided in a single solution containing ethanol or acetone or other suitable solvents. Methods according to the present invention include use of the foregoing novel compositions as a single step for priming and imparting enhanced adhesion between dental substrates and dental restoratives or components without the need for additional layers of unfilled bonding resin.

Compositions and methods according to the present invention (1) simplify application of dental restorative materials or components through elimination of primer mixing steps immediately before application to the substrate and/or the separate steps of application of a primer and subsequent application of an adhesive to the chosen substrate, (2) provide high bonding strengths between the substrate and restoratives or devices, and (3) allow light-curing of the primer/bonding-resin composition and subsequent application of a self-curing, light-curing or dual-curing composite restorative composition. Surprisingly, preferred compositions and methods of the present invention exhibit high bond strengths even when packaged together in a single solution and stored over considerable periods of time, permitting formulation of the compositions well in advance of the time of their intended application.

Other objects and advantages of the invention will be apparent to those skilled in the art from the following detailed description, taken in conjunction with the appended claims.

DETAILED DESCRIPTION OF THE PREFERRED EMBODIMENTS OF THE INVENTION

The presently preferred compositions of the present invention comprise compositions containing (a) a polymerizable resin component; (b) a photo-initiator system; and (c) a solvent. According to the invention, the components (a), (b), and (c) are selected so that upon mixing of the components, the substantial polymerization of the resin component (a) results only upon exposure of the mixture to either activating radiation or another polymerization catalyst.

The polymerizable resin component according to the invention includes a mixture of (i) at least one hydrophilic primer monomer such as biphenyl dimethacrylate (BPDM) and other hydrophilic monomers which are the reaction products of anhydrides or dianhydrides with a compound having at least one vinyl group and at least one hydroxyl group such as 2-hydroxyethyl methacrylate (2-HEMA); (ii) high viscosity adhesive resins such as Bis-GMA, the reaction product of methacrylic acid and diglycidyl ether of bisphenol A, urethane dimethacrylate UDMA) and/or dipentaerythritol pentacrylate (DPEPA); and (iii) one or more reactive diluent monomers such as 2-HEMA, glycerol monomethacrylate and/or hydroxypropyl methacrylate (HMPA).

The photo-initiator system according to the invention includes a light-sensitive initiator compound, preferably camphorquinone (CQ) or CQ derivatives and a polymerization accelerator compound for initiating polymerization of the resin component. The accelerator compound is activated by the light-sensitive initiator compound to a state which causes polymerization of the resin component. The accelerator compound is preferably a tertiary aromatic amine compound having the formula

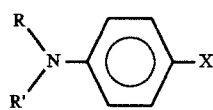

wherein R and R' may be the same or different and may be either $C_1$–$C_3$ alkyl, $C_1$–$C_3$ alkyl alcohol, or $CN(CH_2)_n$ wherein n is 1, 2, or 3 and X is an electron-withdrawing substituent. Preferably, X is selected from COOH, alkali metal salts of COOH, COOR" wherein R" is an alkyl group, $SO_3H$, salts of $SO_3H$, CHO, halogen atoms, $CH_2COOH$, salts of $CH_2COOH$, and CN.

The accelerator compound may also be a cyclic amine compound having the formula

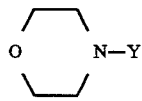

wherein Y is selected from the following: $CH_2CH_2Z$, $CH_2CH_2CH_2Z$, and $CH_2CH(CH_3)Z$ wherein Z is selected from acrylates, methacrylates, alcohols, carboxylic acids, derivatives of carboxylic acids, halogens, and other substituents which do not prevent polymerization of said resin component. Preferably, Y is either ethyl methacrylate or isopropyl methacrylate. Preferably, such cyclic amine compounds comprise from about 0.01 wt. % to about 10 wt. %, and more preferably from about 0.05 wt. % and about 5 wt. %, and presently most preferably from about 0.1 wt. % to about 2 wt. % of the total composition.

According to the invention, the resin component and the photo-initiator system are supplied as a mixture in a solvent solution containing acetone, ethanol, water or other suitable solvent.

Preferred methods of the present invention include applying a thin layer of the aforesaid preferred primer/bonding-resin composition as one step of a dental restorative process. The applied primer/bonding-resin is then preferably cured to a solid state, preferably with an appropriate visible light source. A composite resin or other dental restorative resin or component may then be applied to the cured primer/bonding-resin layer and preferably bonded to that layer by copolymerization through light-curing or self-curing.

Preferably, application of the combined primer/bonding-resin composition of the present invention to tooth dentin and/or enamel substrates is preceded by the step of "etching" or decalcifying the substrate with an acidic solution. Such acidic pretreatment steps are well-known in the art. The acidic solution removes the smear layer present on cut dentin substrate and/or etches the tooth enamel substrate, opening microtubules in the dentin and spaces in the enamel. Those openings may be penetrated by the primer/bonding composition.

Thus a preferred embodiment of the present invention includes an initial acid etching step of the dental substrate followed by the step of application and partial cure of the one component primer/bonding-resin composition, followed by application and bonding of the dental restorative or luting composite.

Presently preferred hydrophilic monomers of the present invention include BPDM, one of the primers disclosed and claimed in U.S. Pat. No. 5,348,988, which patent is assigned to the assignee of the present application and the disclosure of which is hereby incorporated by reference. As indicated in Example 1 of the '988 patent, BPDM is the reaction product of an aromatic dianhydride with an excess of 2-HEMA (2-hydroxyethyl methacrylate). Other presently preferred hydrophilic monomers of the present invention include EDMT, the reaction product of 2-HEMA with ethylene glycol bistrimellitate dianhydride, DSDM, the reaction product of 3,3',4,4'-diphenylsulfone tetracarboxylic dianhydride and 2-HEMA, PMDM, and PMGDM, the adduct reaction product of pyromellitic dianhydride with 2-HEMA and glycerol dimethacrylate, respectively, and other reaction products of anhydride/dianhydride compounds with 2-HEMA, and mixtures of two or more of the foregoing reaction products.

Preferred hydrophilic monomers of the present invention contain groups to enhance hydrophilicity, such as carboxylic acid groups, and contain polymerizable groups such as reactive vinyl (C=C) groups. Such hydrophilic polymerizable monomers are preferably present in the composition in a concentration range of from about 0.5 wt. % to about 50 wt. %, more preferably in the range from about 2 wt. % to about 40 wt. %, and presently most preferably in the range of from about 5 wt. % to about 30 wt. % of the total composition, depending in part on the relative amount of other resins and solvent(s) present in the composition.

Presently preferred high viscosity bonding resin monomers according to the present invention include the diglycidyl methacrylate adduct of Bisphenol A (Bis-GMA), dipentaerythritol pentaacrylate (DPEPA), pentaerythritol dimethacrylate (PEDM), urethane dimethacrylate (UDMA)

and mixtures of one or more of these or other high viscosity adhesive monomers containing reactive vinyl (C=C) groups. Such high viscosity monomers are useful in preparing combined primer/bonding-resin solutions according to the present invention which possess sufficient viscosity such that they can be applied in one or a relatively few number of coats and achieve a uniform thin coating of the dental substrate, while providing high bonding strengths between the dental substrate and the restorative material or dental component.

Presently preferred concentrations of the aforementioned high viscosity adhesive monomer resins are from about 0.5 wt. % to about 50 wt. %, more preferably from about 1 wt. % to about 30 wt. %, and presently more preferably from about 5 wt. % to about 15 wt. % of the total solution. The amount of such high viscosity monomers is preferably selected such that the overall primer/bonding-resin solution has sufficient viscosity to be applied in a relatively few number of coats to achieve a uniform thin layer on the dental substrate, i.e. preferably three or less coats, and more preferably one or two coats. The amount of such high viscosity primer is also selected by also considering the amount of solvent, hydrophilic monomer and low viscosity reactive monomer so as to also permit penetration of the primer/bonding-resin solution into the dental substrate. Preferably, the total resin content of compositions of the present invention are from about 2 wt. % to about 70 or 80 wt. % of the total solution, the remainder comprising one or more of the aforementioned preferred solvents and photo-initiator systems identified below.

Presently preferred low viscosity reactive diluent monomers according to the present invention include 2-HEMA, glycerol monomethacrylate (GM) and hydroxypropyl methacrylate (HPMA) and other monomers containing one or more functional hydroxy groups and reactive vinyl groups. The low viscosity monomers are preferably present in the composition in from about 0.5 wt. % to about 50 wt. %, more preferably from about 1 wt. % to about 30 wt. %, and presently most preferably from about 5 wt. % to about 25 wt. % of the total composition. As indicated below, the preferred concentration of such low viscosity monomers depends in part on the particular high viscosity adhesive monomer selected for use in the invention, as well as the mount of hydrophilic monomer and solvents used in the composition. The low viscosity monomers of the present invention, together with the other components of the system, are preferably intended to promote penetration of the primer/bonding-resin composition into the openings created by abrading or decalcifying (etching) tooth dentin and/or enamel or other substrates to assist in formation of strong adherence between the primer/bonding-resin and the dental substrate.

Photo-initiator systems according to preferred embodiments of the present invention include alpha-diketone fight-sensitive initiator compounds such as camphorquinone (CQ) and CQ derivatives and certain tertiary aromatic amine polymerization accelerator compounds. Preferably, photo-initiator systems according to the invention are sensitive to visible light and possibly into a range of other wavelength light that is not harmful to a patient undergoing a dental procedure. Some compounds that may be suitable ultraviolet light-sensitive initiators are 1,2-diketones, benzophenones, substituted benzophenones, benzoin methyl ether, isopropoxybenzoin, benzoin phenyl ether, and benzoin isobutyl ether.

Preferred tertiary amine compounds according to the invention include tertiary aromatic amine compounds having the formula

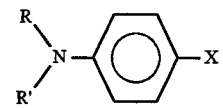

wherein R and R' are preferably selected from the group $CH_3$, $CH_2CH_3$, and $CH_2CH_2CH_3$ and X is an electron withdrawing substituent preferably selected from the following: COOH, alkali metal salts of COOH, COOR" wherein R" is an alkyl group ($C_nH_{2n+1}$) $SO_3H$, salts of $SO_3H$, CHO, halogen atoms, $CH_2COOH$, salts of $CH_2COOH$, and CN.

Presently preferred CQ or CQ derivative concentrations range from about 0.01 wt. % to about 5 wt. %, more preferably from about 0.05 wt. % to about 2 wt. %, and presently most preferably from about 0.1 wt. % to about 1.0 wt. % of the total composition. Presently preferred concentrations of tertiary aromatic amine compounds of the present invention of the formula identified above are from about 0.01 wt. % to about 10 wt. %, more preferably from about 0.05 wt. % to about 5 wt. % and presently most preferably from about 0.1 wt. % to about 2 wt. % of the total composition. The amount of each component of the photo-initiator system depends in part on the amount of monomer resin present in the solution whose polymerization is to be catalyzed. Particularly preferred photo-initiator systems include CQ and dimethylaminobenaldehyde (DMABAL) or dimethylaminobenzoic acid (DMABA).

The following Examples showing presently preferred embodiments of the present invention are for illustrative purposes only, and in no way should be construed as limiting the present invention.

EXAMPLE 1

Preparation of Hydrophilic Monomers

BPDM monomer synthesis: The biphenyl dimethacrylate monomer was prepared according to the method of Example 1 of U.S. Pat. No. 5,348,988. Symmetrical biphenyl tetracarboxylic dianhydride (s-BPDA, Chriskev Co., Leawood, Kans.), 58.8 g (0.2 mole), was weighed into a flask, 2-hydroxyethylmethacrylate (2-HEMA), 78.1 g (0.6 mole) was added together with 5 ml of triethylamine. The mixture was stirred and heated at 80°–90° C. for one hour, during which time a clear solution resulted. At this time, the infrared spectrum of the product revealed the disappearance of the anhydride absorption bands.

EDMT monomer synthesis: This monomer was prepared according to the procedure used to prepare BPDM set out above, but the starting dianhydride for EDMT is ethyleneglycol bistrimellitate dianhydride (TMEG-200, Chriskev Co., Leawood, Kans.). 0.40 mole of TMEG-200 and 1.00 mole of 2-HEMA were used for the synthesis of EDMT monomer according to that procedure.

Other hydrophilic monomers used in the following examples and the other compounds identified herein are compounds purchased from the manufactures indicated in the following list, which list also includes the abbreviations used herein to identify those compounds.

| | |
|---|---|
| Acetone | (Ashland Chemical Inc.). |
| BisGMA | Diglycidylmethacrylate adduct of Bisphenol A (Cook Composites and Polymers). |
| BPDM | Adduct of 3,3',4,4'-diphenyl tetracarboxylic dianhydride and 2-hydroxyethyl methacrylate (Bisco, Inc.). |
| Br-DMA | p-Bromo-N,N-dimethylaniline (TCI America). |

-continued

| | |
|---|---|
| CQ | Camphorquinone (Hampford Research, Inc.). |
| DMABA | Dimethylaminobenzoic acid (TCI America). |
| DMABAL | Dimethylaminobenzaldehyde (TCI America). |
| DMAEMA | Dimethylaminoethyl methacrylate (Rocryl 700, Rohm & Haas Co.). |
| DPEPA | Dipentaerythritol Pentaacrylate (Monomer-Polymer & Dajac Laboratories, Inc.). |
| DSDM | Adduct of 3,3', 4,4'-biphenylsulfone tetracarboxylic dianhydride and 2-hydroxyethyl methacrylate (Bisco, Inc.). |
| EDMAB | Ethyl dimethylaminobenzoate (Lancaster). |
| EDMT | Adduct of ethylene glycol bistrimellitate dianhydride and 2-hydroxyethyl methacrylate (Bisco, Inc.). |
| EtOH | Ethanol (AAPER Alcohol & Chemical Co.). |
| GM | Glycerol mono-methacrylate (Monomer-Polymer & Dajac Laboratories, Inc.). |
| 2-HEMA | 2-Hydroxyethyl methacrylate (Rohm & Haas Co.). |
| HPMA | Hydroxypropyl methacrylate (Rohm & Haas Co.). |
| MEHQ | 4-Methoxyphenol (Aldrich Co.) |
| MEM | 2-N-Morpholinoethyl methacrylate (Rohm Tech Inc.). |
| PEDM | Pentaerythritol dimethacrylate (Monomer-Polymer & Dajac Laboratories, Inc.). |
| PMDM | Adduct of pyromellitic dianhydride and 2-hydroxy methacrylate (Esschem Co.). |
| PMGDM | Adduct of pyromellitic dianhydride and glycerol dimethacrylate (Esschem Co.). |
| UDMA | Urethane dimethacrylate (Esschem Co.). |

EXAMPLE 2

Formulation of Primer/bonding-resin Compositions

The following method was used to prepare the primer/bonding-resin compositions set out in the following Examples 4–29.

Fifty (50) gram primer\bonding-resin compositions were prepared containing the weight percent of each component identified in the formulations in Examples 4–29 by weighing out in grams one-half of the indicated weight percent for that component. The procedure for preparation of the composition consisted of three mixing steps.

First, the hydrophilic monomer(s), reactive diluent monomers and high viscosity monomers (component (a)) were combined in a 100 ml beaker in the appropriate weight of solvent (component (c)) comprising ethanol (15%, formulation 3C, AAPER, Columbus Ohio) and/or acetone (42.75%, ACS grade, Ashland Chemical, Inc. Columbus, Ohio) and/or water and mixed with a magnetic stir bar until all monomers dissolved (approximately one/half hour.) An appropriate weight amount of tertiary amine catalyst, component (b)(1) in solution was then added to the beaker and mixed for about 15 minutes.

In the third step, an appropriate weight amount of photo-initiator component (b)(2) comprising CQ or a CQ derivative was added to the beaker in a dark room to shield it from ambient light. The beaker was then wrapped with aluminum foil to further exclude ambient light and the contents mixed as before but for 20 minutes. The resultant solution was poured into opaque plastic bottles and stored for future use.

EXAMPLE 3

Bonding Strength Test Methods

The following test methods were employed in all the Examples 4–29 to determine the shear bonding strengths of the indicated primer/bonding-resin on the indicated substrates.

Dentin Shear Bond Strength Test Procedure:

Extracted human teeth were embedded in resin discs, abraded on the facial surface with a model trimmer, and subsequently abraded with wet 600 grit SiC paper to create a flat and smooth dentin substrate for bonding. The dentin surfaces were then etched using All-Etch (BISCO, Inc.) (10% $H_3PO_4$) or Uni-Etch (32% $H_3PO_4$) for 15 seconds and rinsed with water for 10 seconds. Excess water on the tooth surface was blotted off with Kimwipes® or the dentin surface was flash-dried for 1–2 seconds with an air syringe to obtain a moist dentin surface for bonding. 2–3 coats of the chosen one-component primer/bonding-resin composition (or other primer systems as indicated in the example) were applied by brush to the dentin within about 5–6 seconds to achieve a uniform layer of the primer/bonding-resin. The primer/bonding-resin composition was gently dried with an air syringe for about 10 seconds, and then light cured for 10 seconds using an Optilux® 400 curing lamp (Demetron Research Corp., Danbury, Conn.). BIS-FIL® (Bisco) Light-Cure Composite was condensed into a #5 gelatin capsule post which was partially ($\frac{2}{3}$) fried with the cured same composite. The completely fried capsule was then placed onto the prepared dentin surface and the excess composite was removed with a Hollenback carver while the post was held in place with gentle finger pressure. The composite was photo-cured for 40 seconds using the above-identified lamp. Samples were stored in water at 37° C. for 2 hours before being debonded in shear with a knife edge on an Instron model 1133 machine at a crosshead speed of 0.5 mm/min. Shear bond strength was calculated in MPa by dividing the peak load by bonding area. The mean and standard deviations for bond strength were calculated from five replications for each formulation.

Enamel Shear Bond Test Procedure.

Adhesive shear bond strengths of primer/bonding-resin compositions to tooth enamel were determined by the procedure used for determining dentin shear bonding strengths set out above with the following modifications:

First, extracted teeth were imbedded to a lesser depth in the acrylic resin to permit better exposure of the enamel surface. Second, enamel surfaces were etched by application of UNI-ETCH 32% $H_3PO_4$ solution (Bisco, Inc.) Third, two coats of the desired primer/bonding-resin composition (or other primer systems as indicated in the Examples) were applied. Cure of the applied primer/bonding-resin composition(s), application and cure of composite and shear bond strengths were carried out according to the same procedures used for the dentin shear bond strength test procedures.

Metal and Ceramic Substrates Shear Bonding Test Procedures.

The following test protocols were employed to examine the bonding strengths of compositions of the present invention to non-precious metal alloys, precious metals and other metal substrates.

(1) Substrate Preparation. The substrates for the ceramic and metal substrate bonding test were prepared by imbedding cast metal or metal and ceramic cylinders in acrylic resin discs. The metal and/or ceramic surfaces of the disks were treated as follows prior to application of the primer/bonding-resin composition. First the exposed disk face was polished with SiC paper, #320 and #600 grit, sequentially to create a flat fresh surface. That polished surface was then sandblasted with aluminum oxide (50 micron), and then rinsed and dried. Unless indicated otherwise below, the following bonding protocol was then used to examine bond strengths of the following substrates.

(2) Bonding to Non-Precious Alloys. A non-precious metal alloy substrate, REXILLIUM III, (a commercial product of Jeneric/Pentron Inc., Wallingford, Conn. containing 74–78% Ni, 12–14% Cr, 4–6% Mo and a maximum of 1.8% Be and 2.5% Al) was selected for examination of shear bond strengths of various preferred primer/bonding-resin compositions of the present invention.

A disk of REXILLIUM III cast, polished and prepared according to the foregoing procedure. Unless otherwise indicated in a specific example below, the chosen primer/bonding-resin composition or selected two-component primer composition was then applied in 2 coats to the substrate and light-cured for 10 seconds using an Optilux® 400 curing lamp (Demetron Research Corp., Danbury, Conn.). Also, because metallic restoratives are typically dark in color they are typically overlayed with another coloring compound which more closely matches the tooth color and enhances the appearance of the final restoration. A commercial coloring product (BISCO Dual-Cure Opaquer) was applied to the applied, partially cured primer/bonding-resin or partially cured two-component primer layer and the Opaquer cured according to the manufacturer's instructions (40 second self-cure followed by 10 second light cure). A commercial unfilled dentin/enamel resin (Bisco Dentin/Enamel unfilled bonding resin) was coated on the Opaquer layer and a commercial composite material (Bisco BIS-FIL® Light-Cure Composite) was coated thereon and light-cured for 40 seconds.

Shear bond strengths for the various primer compositions were determined using the Instron machine and procedures set out above for determining dentin and enamel shear bond strengths.

(3) Bonding to Precious Metals and other Substrates. Gold alloy and stainless steel substrates were prepared as indicated above and shear bond strengths for composition bonding to these substrates were examined using the procedure set out above for examining bond strengths to nonprecious metal alloys.

EXAMPLE 4

In this Example and the following Examples primer/bonding-resin compositions were formulated by admixing (a) resin monomer compounds; (b)(1) polymerization accelerator compounds; (b)(2) light-sensitive initiator compounds; and (c) solvents according to their indicated weight percentages using the procedure of Example 2. Substitutions for some of those components are indicated in the formulation for a given Example.

Shear bonding strengths of the formulated compositions to various substrates were examined in this and the following Examples according to the procedure of Example 3. Stability of the compositions were also examined by measuring bonding strengths after storage of the composition at the indicated temperature for the indicated time. Storage at 37 degrees centigrade for 1–3 months approximates about 3 to 4 months to about 1 year or more of storage at room temperature (R.T.).

Formulation 1: (a) BPDM 10.0, EDMT 10.0, 2-HEMA 13.0 BisGMA 8.0; (b)(1) DMABA 1.0; (b)(2) CQ 0.25; (c) Ethanol 19.75, and Acetone 35.0.
Dentin shear bond strength:

Fresh formulation: 25.7±2.4 MPa 1 month at R.T.: 28.8±2.4 MPa 2 months at R.T.: 25.8±1.9 MPa 3 months at R.T.: 21.7±2.3 MPa 4 months at R.T.: 23.3±1.8 MPa 1 month at 37° C.: 25.5±2.8 MPa 2 months at 37° C.: 16.7±1.9 MPa Enamel shear bond strength:
Fresh formulation: 26.7±4.7 MPa

EXAMPLE 5

Formulation 2: (a) BPDM 10.0, EDMT 10.0, 2-HEMA 13.0, BisGMA 8.0; (b)(1) DMABAL 1.0; Co)(2) CQ 0.25; (c) EtOH 15.0, Acetone 42.75. Bonding strengths to various substrates for this formulation were as follows:
Dentin:

Initial 25.6±2.1 MPa 1 month at R.T. 28.4±2.5 MPa 1 month at 37° C. 22.1±2.4 MPa 2 months at 37° C. 18.4±1.3 MPa Metal (initial):

Stainless Steel: 32.4 (1.9) MPa

REXILLIUM III: 29.8 (3.7) MPa

Gold: 21.0 (5.3) MPa

EXAMPLE 6

Formulation 3: (a)BPDM 10.0, EDMT 10.0, 2-HEMA 13.0, BisGMA 8.0; (b)(1) EDMAB 1.0; (b)(2) CQ 0.25; (c) Ethanol 19.75, and Acetone 35.0.
Dentin shear bond strength:

Fresh formulation: 29.8±3.5 MPa 1 month at R.T.: 26.1±4.3 MPa 2 months at R.T.: 26.8±2.0 MPa 3 months at R.T.: 18.6±2.9 MPa 4 months at R.T.: 25.9±1.8 MPa 1 month at 37° C.: 21.0±3.5 MPa 2 months at 37° C.: 16.4±1.9 MPa

EXAMPLE 7

Formulation 4: (a)BPDM 10.0, EDMT 10.0, 2-HEMA 13.0, BisGMA 8.0; Br-DMA 1.0; (b)(2) CQ 0.25; (c) Ethanol 19.75, and Acetone 35.0.
Dentin shear bond strength:

Fresh formulation: 25.7±2.9 MPa 1 month at R.T.: 24.3±4.1 MPa 2 months at R.T.: 19.9±5.9 MPa 1 month at 37° C.: 20.0±1.8MPa 2 months at 37° C.: 8.0±3.7MPa

EXAMPLE 8

Formulation 5: (a) BPDM 5.0, 2-HEMA 15.0, BisGMA 15.0; (b)(1) EDMAB 1.0; (b)(2) CQ 0.25; (c) Ethanol 15.0, and Acetone 48.75.
Dentin shear bond strength:

Fresh formulation: 29.6±4.0 MPa 1 month at R.T.: 26.6±5.6 MPa 2 months at R.T.: 24.8±6.9 MPa 3 months at R.T.: 23.8±2.2 MPa 4 months at R.T.: 22.1±3.7 MPa 1 month at 37° C. 21.9±3.8 MPa 2 months at 37° C.: 20.6±4.1 MPa

EXAMPLE 9

Formulation 6: (a) BPDM 1.0, 2-HEMA 15.0, BisGMA 15.0; (b)(1) DMABAL 1.0; (b)(2) CQ 0.25; Acetone 67.75.
Dentin shear bond strength:

Fresh formulation: 22.2±4.0 MPa

EXAMPLE 10

Formulation 7: (a) 2-HEMA 15.0, BisGMA 15.0; (b)(1) DMABAL 1.0; (b)(2) CQ 0.25; Acetone 68.75.
Dentin shear bond strength:
Fresh formulation: 16.4±4.2 MPa

EXAMPLE 11

Formulation 8: (a) BPDM 20.0, 2-HEMA 13.0, BisGMA 8.0; (b)(1) DMABAL 1.0; (b)(2) CQ 0.25; (c) Ethanol 15.0, and Acetone 42.75.
Dentin shear bond strength:
Fresh formulation: 24.0±2.3 MPa
1 month at R.T.: 26.9±2.2 MPa
1 month at 37° C.: 23.2±1.9 MPa
2 months at 37° C.: 19.5±2.2 MPa

EXAMPLE 12

Formulation 9: (a) BPDM 10.0, EDMT 10.0, 2-HEMA 15.0, BisGMA 8.0; MEM 4.0; (b)(2) CQ 0.25; Ethanol 17.75, and Acetone 45.0.
Dentin shear bond strength:
Fresh formulation: 29.0±3.7 MPa
1 month at R.T.: 24.9±3.5 MPa
2 months at R.T.: 22.5±2.5 MPa
3 months at R.T.: 16.8±1.5 MPa
1 ∞months at R.T.: 13.2±2.7 MPa
1 month at 37° C.: 12.1±4.4 MPa
2 months at 37° C.: 7.9±2.0 MPa

EXAMPLE 13

Formulation 10: (a) BPDM 10.0, EDMT 10.0, 2-HEMA 13.0, BisGMA 8.0; DMAEMA 1.0; (b)(2) CQ 0.25: (c) Ethanol 22.75, and Acetone 35.0.
Dentin shear bond strength:
Fresh formulation: 3.1±1.0 MPa.

EXAMPLE 14

Formulation 11: (a) BPDM 16.0, 2-HEMA 15.0, BisGMA 10.0; (b)(1) DMABAL 1.0; Co)(2) CQ 0.25; (c) Acetone 57.75.
Dentin shear bond strength:
Fresh formulation: 25.7±3.6 MPa
1 month at R.T.: 22.9±5.1 MPa
2 months at R.T.: 24.9±3.7 MPa
3 months at R.T.: 23.4±2.0 MPa
4 months at R.T.: 22.5±2.7 MPa
1month at 37° C.: 21.5±6.2 MPa
2 months at 37° C.: 20.5±7.1 MPa
3 months at 37° C: 25.1±3.1 MPa

EXAMPLE 15

Formulation 12: (a) PMGDM 16.0, 2-HEMA 15.0, BisGMA 10.0; (b)(1) DMABAL 1.0; Co)(2) CQ 0.25: (c) Ethanol 15, Acetone 42.75.
Dentin shear bond strength:
Fresh formulation: 22.4±4.0 MPa.

EXAMPLE 16

Formulation 13: (a) BPDM 12.0, 2-HEMA 11.0, BisGMA 11.0; DMABA 1.0; (b)(2) CQ 0.25; (c) Ethanol 10.0, and Acetone 54.75.
Dentin shear bond strength:
Fresh formulation: 26.2±6.8 MPa.
1 month at 37° C.: 23.8±5.2 MPa
2 months at 37° C.: 20.0±0.7 MPa

EXAMPLE 17

Formulation 14 (a): (a) BPDM 6.0, EDMT 6.0, 2-HEMA 11.0, BisGMA 11.0; (b)(1) DMABA 1.0; (b)(2) CQ 0.25; (c) Ethanol 10.0, Acetone 54.75, and MEHQ 0.01.
Dentin shear bond strength:
Fresh formulation: 23.6±4.0 MPa
1month at 37° C.: 23.8±0.8 MPa
2months at 37° C.: 19.4±3.6 MPa
Formulation 140(b): (a) BPDM 6.0, EDMT 6.0, 2-HEMA 11.0, BisGMA 11.0; (b)(1) DMABA 1.0; (b)(2) CQ 0.25; (c) Ethanol 10.0, and Acetone 54.75.
Dentin shear bond strength:
Fresh formulation: 24.1±2.8 MPa
1 month at 37° C.: 22.2±4.2 MPa
2 months at 37° C.: 20.9±2.5 MPa

EXAMPLE 18

Formulation 15: (a) EDMT 20.0, 2-HEMA 15.0, BisGMA 8.0; MEM 5.0; (b)(2) CQ 0.25; (c) Ethanol 36.75, and Acetone 15.0.
Dentin shear bond strength:
Fresh formulation: 28.1±2.4 MPa.

EXAMPLE 19

Formulation 16: (a) BPDM 10.0, EDMT 10.0, 2-HEMA 13.0, UDMA 8.0; 00)(1) DMABA 1.0; (b)(2) CQ 0.25; (c) Ethanol 22.75, and Acetone 35.0.
Dentin shear bond strength:
Fresh formulation: 28.0±4.2 MPa.

EXAMPLE 20

Formulation 17: (a) BPDM 10.0, EDMT 10.0, 2-HEMA 13.0, DPEPA 8.0; (b)(1) DMABA 1.0; (b)(2) CQ 0.25; (c) Ethanol 22.75, and Acetone 35.0.
Dentin shear bond strength:
Fresh formulation: 23.3±2.4 MPa.

EXAMPLE 21

Formulation 18: (a) BPDM 10.0, EDMT 6.0, HPMA 13.0, BisGMA 8.0: (b)(1) DMABA 1.0; (b)(2) CQ 0.25; (c) Ethanol 21.75, and Acetone 40.0.
Dentin shear bond strength:
Fresh formulation: 26.0±1.7 MPa.

EXAMPLE 22

Formulation 19: (a) BPDM 10.0, EDMT 6.0, GM 13.0, BisGMA 8.0; (b)(1) DMABA 1.0; (b)(2) CQ 0.25; (c) Ethanol 21.75, and Acetone 40.0.
Dentin shear bond strength:
Fresh formulation: 25.0±1.0 MPa.

EXAMPLE 23

Formulation 20: (a) BPDM 18.0, 2-HEMA 18.0, BisGMA 6.0; (b)(1) DMABAL 1.0; (b)(2) CQ 0.25; Acetone 56.75.
Dentin shear bond strength:
Fresh formulation: 28.1±1.9 MPa

EXAMPLE 24

Formulation 21: (a) BPDM 20.0, 2-HEMA 0.0 (approximately 3.8 due to excess 2-HEMA used in BPDM synthesis), BisGMA 6.0; (b)(1) DMABAL 1.0; (b)(2) CQ 0.25; Acetone 72.75.

Dentin shear bond strength:

Fresh formulation: 22.5±3.3 MPa

EXAMPLE 25

To illustrate that other commercial composite products on the market can be used with applicants' primer/bonding-resin compositions for bonding to dentin, the composition of Example 4 was tested for dentin shear bond strength using a commercial brand composite, Herculite XRV (Kerr) as a substitute for BIS-FIL® Composite (Bisco). An excellent dentin shear bond strength of 23.6±1.7 MPa was obtained with Herculite XRV Composite. It is expected that other commercial composites will also function well with applicants' primer/bonding-resin compositions and methods.

EXAMPLE 26

Adhesion enhancement of the formulation of Example 4 was examined relative to non-primer systems based on applicants' assignees' two-component primer commercial product. REXILLIUM III was selected as the ceramic alloy substrate for this examination. The procedure of Example 3 were followed for initial substrate preparation.

Applicants' Example 4 composition and the following materials were applied to separate REXILLIUM III alloy substrate disks according to the following protocols.

(a) One coat of Bisco's All-Bond 2® Dentin/Enamel Bonding Resin (D/E resin) was applied to the substrate and light-cured for 10s using an Optilux® 400 curing lamp (Demetron Research Corp., Danbury, Conn.). Bisco's BIS-FIL® Light-Cure Composite was then applied, light-cured (L/C) for forty seconds and shear bond strength was evaluated using the procedure of Example 3.

(b) Formulation 1 of Example 4 was applied to the substrate in two coats and light-cured for 10 seconds. Bisco's BIS-FIL® Light-Cure Composite was applied, cured for 40 seconds and shear bond strength was evaluated according to the procedure of Example 3.

(c) The procedure of Example 3 for evaluating bond strengths of formulations using Bisco Opaquer was also carried out using the primer/bonding-resin formulation of Example 4.

The bonding strengths to REXILLIUM III for the three protocols set forth above are listed in the following Table I.

TABLE I

Shear Bond Strengths (SBS) - Selected Protocols

| No. | Bonding Procedures | SBS (MPa) |
|---|---|---|
| a | D/E bonding resin (L/C), BIS-FIL ® Composite (L/C) | 14.9 ± 2.0 |
| b | Priming Resin (L/C), BIS-FIL ® Composite (L/C) | 20.3 ± 1.2 |
| c | Priming Resin (L/C), Opacquer (D/C), D/E resin (no curing), BIS-FIL ® Composite (L/C) | 28.2 ± 2.0 |

Protocol (b) using a applicants' primer/bonding-resin composition showed significant improvement over protocol (a) using only a Dentin/Enamel Resin. Utilization of an Opacquer layer in protocol (c) further increased bonding strength to 28.2 MPa, an extremely high value rarely achievable with any dental adhesive system for metal bonding.

Examination was also made of the bonding of Example 4's formulations to other metal substrates, including precious metal (gold alloy) and stainless steel. Protocol (c) above was used for these examinations, with tests made on REXILLIUM III substrate as well as on gold alloy and stainless steel substrates. The resultant shear bond strengths are listed in Table II below:

TABLE II

Shear Bond Strengths (SBS) - Selected Metals

| No. | Metal Substrate | SBS (MPa) |
|---|---|---|
| 1 | REXILLIUM III | 28.2 ± 2.0 |
| 2 | Stainless Steel | 28.2 ± 1.7 |
| 3 | Gold Alloy | 24.2 ± 2.1 |

The Example 4 composition yielded excellent bonding results for all the metal substrates tested.

EXAMPLE 27

The following tables show the results of an aging study on formulations containing different amines at room temperature and 37° C. respectively. Dentin bondings were performed using formulations being aged for different time durations. A primer/bonding-resin composition of the following formulation (and weight percentages) was examined: (a) BPDM 10, EDMT 10, 2-HEMA 13, BisGMA 8; (b)(1) Amine 1.0, (b)(2)CQ 0.25; (c) EtOH 22.75, Acetone 35.0. Formulations of the composition were prepared according to the procedure of Example 2 using each of the following amines as the polymerization accelerator component (b)(1) of the composition (or substitute therefore in the case of DMAEMA), and shear bond strengths were determined as set forth in Example 3.

Aromatic tertiary amines:

| | |
|---|---|
| DMABA | Dimethylaminobenzoic acid (TCI America) |
| DMABAL | Dimethylaminobenzaldehyde (TCI America) |
| EDMAB | Ethyl dimethylaminobenzoate (Lancaster) |

Non-aromatic tertiary amines:

| | |
|---|---|
| MEM | 2-N-Morpholinoethyl methacrylate (Rohm Tech Inc.) |
| DMAEMA | Dimethylaminoethyl methacrylate (Rocryl 700, Rohm & Haas Co.) |

TABLE III

Aging Study of Formulations Containing Different Amines at Room Temp.

| | Dentin Bonding Strength (MPa) | | |
|---|---|---|---|
| Amine | Initial | 1 month | 2 months |
| DMABA | 25.7 ± 2.4 | 28.8 ± 2.4 | 25.8 ± 1.9 |
| DMABAL | 29.1 ± 2.1 | 25.0 ± 4.5 | 24.2 ± 3.5 |
| EDMAB | 29.8 ± 3.5 | 26.1 ± 4.3 | 26.8 ± 2.0 |
| MEM | 29.0 ± 3.7 | 24.9 ± 3.5 | 22.5 ± 2.5 |
| DMAEMA (Rocryl 700) | 3.1 ± 1.0* | — | — |

TABLE IV

Aging Study of Formulations Containing Different Amines at 37° C.

| | Dentin Bonding Strength (MPa) | | |
|---|---|---|---|
| Amine | Initial | 1 month | 2 months |
| DMABA | 25.7 ± 2.4 | 25.5 ± 2.8 | 16.7 ± 1.9 |
| DMABAL | 29.1 ± 2.1 | 24.2 ± 1.5 | 16.0 ± 2.3 |
| EDMAB | 29.8 ± 3.5 | 21.0 ± 3.5 | 16.4 ± 1.9 |
| MEM | 29.0 ± 3.7 | 12.1 ± 4.4 | 7.9 ± 2.0 |
| DMAEMA (Rocryl 700) | 3.1 ± 1.0* | — | — |

*This data was obtained one day after the formulation. The dentin shear bonding strength for priming resin containing DMAEMA immediately after formulation was 2.3 ± 0.4 MPa.

The compositions using the amine polymerization accelerators of the present invention exhibited good stability at room temperature for at least 2 months and at elevated temperatures for at least one month.

EXAMPLE 28

Formulation: DSDM (Bisco, Inc.) was evaluated in the following formulation: (a) DSDM 16, 2-HEMA 15, BisGMA 10; (b)(1) DMABA 1.0; (b)(2) CQ 0.25; (c) EtOH 15, Acetone 42.75. DSDM is the reaction adduct of 3,3',4,4'-diphenylsulfone tetracarboxylic dianhydride and hydroxyethyl methacrylate (2-HEMA). This formulation was formulated and tested according to Examples 2 and 3 and yielded a dentin bonding strength of 22.9±3.0 MPa.

EXAMPLE 29

Various solvents were examined in connection with compositions having the following formulation: (a) BPDM 16.0, 2-HEMA 15.0, BisGMA 10.0; (b)0) DMABA 1.0; (b)(2) CQ 0.25; (c) acetone and ethanol, varied as indicated below to a total of 57.75.

First, anhydrous ethanol at concentrations of 0%, 10% and 15% was admixed with corresponding values of acetone to provide a total solvent weight percentage of 57.75 and used to prepare a composition according to the above formulation. Initial dentin bond strengths for those compositions and a composition using regular (15%) ethanol were examined and compared with bond strengths after 3 months storage at room temperature. The resultant data is set out in the following table.

TABLE V

3-Month Aging Study with Selected Solvents -
Dentin Shear Bonding Strengths (SBS) in MPa
1. Regular EtOH vs. Anhydrous EtOH (15%)
2. Anhydrous EtOH Concentration (15%, 10%, 0%)

| | | Regular EtOH | Anhydrous EtOH | | |
|---|---|---|---|---|---|
| Aging Temp. | Aging Time | 15% | 15% | 10% | 0% |
| Room Temp. | Initial | 28.4 ± 2.0 | 31.5 ± 2.4 | 27.7 ± 1.9 | 25.7 ± 3.6 |
| Room Temp. | 3 mo. | 25.8 ± 1.9 | 27.0 ± 0.8 | 23.7 ± 1.8 | 23.4 ± 2.0 |
| Oven Temp. (37° C.) | 3 mo. | — | — | — | 25.1 ± 3.1 |

Formulations using constant amounts of DMABAL (1.0), CQ (0.5) and where indicated, regular ethanol (15), and varying amounts of resin components and other solvents were prepared according to the following Table VI and examined for initial dentin bond strengths and bond strengths after 1 month storage at 37° C. for 1–2 months. The resultant data is also set forth in the following Table VI.

TABLE VI

Aging Study of Different Formulations
Dentin Shear Bond Strength (SBS) in MPa

| | SBS (MPa) at Room Temp. | | SBS (MPa) at Oven Temp., 37° C. | |
|---|---|---|---|---|
| Formulation[1,2] | Initial | 1 Month | 1 Month | 2 Month |
| A1 | 25.6 ± 2.1 | 28.4 ± 2.5 | 22.1 ± 2.4 | 18.4 ± 1.3 |
| A2 | 24.8 ± 1.6 | | 23.3 ± 2.7 | 17.4 ± 0.8 |
| A3 | 23.9 ± 2.5 | | 24.1 ± 1.9 | 20.3 ± 2.0 |
| B1 | 24.0 ± 2.3 | 26.9 ± 2.2 | 23.2 ± 1.9 | 19.5 ± 2.2 |
| B2 | 25.6 ± 2.7 | | | |
| B3 | 25.9 ± 1.6 | | | |
| C1 | 25.0 ± 4.8 | | 24.9 ± 4.0 | 20.9 ± 2.4 |
| C2 | 24.7 ± 2.7 | | | |
| C3 | 23.4 ± 2.3 | | | |
| D1 | 26.7 ± 5.2 | | 24.7 ± 3.1 | 19.7 ± 3.3 |
| D2 | 24.1 ± 4.1 | | | |
| D3 | 22.5 ± 3.1 | | | |

[1.] BPDM/EDMT/2-HEMA/BisGMA:
Formula A1-3: 10.0/10.0/13.0/8.0;
Formula B1-3: 20.0/0.0/13.0/8.0;
Formula C1-3: 15.0/0.0/15.0/11.0;
Formula D1-3: 10.0/0.0/16.0/15.0.
[2.] Acetone/H$_2$O:
Formula A1, B1, C1, and D1: 42.75/0.0;
Formula A2, B2, C2, and D2: 41.86/0.89;
Formula A3, B3, C3, and D3: 40.08/2.67.
The total (Acetone + H$_2$O) is 42.75.

As shown by the foregoing Examples, compositions and methods according to the present invention simplify the overall restorative process while providing high bond strengths and stable, storable compositions.

Simplification and significant time savings are realized through formulation of applicants' primer/bonding-resin compositions well in advance of use of such compositions on the patient. Such advance formulation can be undertaken by the manufacturer at the plant due to the considerable shelf-life of applicants' compositions. Kits containing those compositions in a single container and/or a separate container of substrate etchant or abrasive are also contemplated as within the scope of applicants' invention.

It is also contemplated that the advantages inherent in applicants' compositions and methods can be realized by formulating applicants' compositions in two parts and in placing those parts into kits containing two separate containers, the contents of which would be admixed by the dental professional in his or her office. The advantages of simplification and expeditious patient treatment could be realized by the manufacturer supplying the two container formulations in mounts whereby their admixture can be conducted on a large scale, i.e. in amounts sufficient to treat two or more patients. Treatment time can be minimized because such compositions may be mixed at convenient times well before the first patient is in the office, and the mixture simply stored in the office in a non-light permeable vessel and used as needed. One container would preferably contain the polymerization acceleration compound and the other container will preferably contain the hydrophilic monomers according to the present invention. One or both of such containers will also contain the other components according to the present invention.

Simplification of patient treatment is made possible by the overall stability exhibited by the compositions of the present invention. As indicated above and in the foregoing Examples, compositions according to the present invention are "shelf-stable", i.e., they exhibit high bond strengths over at least about one month storage at room temperature. Presently preferred compositions are stable for more than one month at room temperature, i.e., up to about 3–4 months, and also exhibit good bond strengths over 1–3 months of storage at elevated temperatures of 37 degrees Centigrade, which are believed to approximate from about 4 months to about one year or more stability at room temperatures. Such enhanced stability permits pre-formulation of applicants' compositions and their use in applicants' claimed methods wherein the dental professional need not step away from each patient to mix primer components, expediting the treatment process. Compositions and methods of the present invention can also be used in indirect procedures, such as the seating of inlays, onlays and crowns, permitting the dental professional to chose the best curing procedure for the clinical picture. Compositions and methods of the present invention are also contemplated wherein only a few, i.e., about 2 to 3 coating steps are necessary to apply the composition to the substrate and adequately prime and impart improved adhesion to that substrate, saving further patient time and professional time and effort.

The exact mechanism by which the present invention achieves its highly beneficial results is not completely known. At present, applicants believe that the combination of their hydrophilic monomers, reactive diluent monomers and bonding resins with a photo-initiator system according to the invention in the indicated solvents prevent degradation of the photo-initiator system as well as premature polymerization, leading to the above-indicated long shelf life. Such prevention of degradation and premature polymerization may also be due to stabilization of the tertiary amine in the accelerators of the present invention by their adjacent moieties including electron-withdrawing groups which comprise and/or are attached to such moieties, making the tertiary amine less basic in a Lewis acid/base sense.

The improved bond strengths of the present invention relative to other systems is also presently believed to result in part from the use of applicants' aforesaid photo-initiator system with applicants' hydrophilic monomers in combination with the reactive diluent monomers and high viscosity bonding resins. That combination is believed to achieve both good subsurface penetration of applicants' primer/bonding-resin compositions into etched dentin and enamel and formation of a relatively uniform primer/bonding-resin layer on the surface of the substrate. Such subsurface penetration is believed important in achieving strong mechanical and/or chemical bonding between the primer/bonding-resin composition and tooth dentin and enamel when the primer/bonding-resin composition is initially at least partially cured, while the uniform coating of the substrate surface facilitates strong bonding between the primer/bonding-resin composition and applied composite resins or other dental components when they are applied and cured into place. Such a uniform layer is also presently believed to facilitate the presence of an oxygen-inhibited, partially uncured surface layer in the applied primer/bonding-resin composition. The partially uncured surface layer, when over-coated with an applied composite or component, and subjected to exposure to additional light and/or an appropriate chemical polymerization catalyst, is believed to undergo additional curing, resulting in strong adherence between the primer/bonding-resin layer and the added composite or component.

Consistent with the foregoing, other hydrophilic monomers, reactive diluent monomers and high viscosity resins are contemplated as within the scope of the present invention. Such compounds are well known to those skilled in the art. Also contemplated are various derivatives of applicants' photo-initiator system compounds, such including without limitation, well-known derivatives of CQ. Those of skill in the art will also appreciate that applicants' preferred solvents may include combinations of various concentrations of other well-known solvents which are appropriate for the monomers and resins of the present invention, such as water and other volatile solvents, together with or possibly in place of some or all of applicants' presently preferred ethanol and/or acetone solvents.

Formulations of other stable primer/bonding-resin compositions according to the present invention will also be apparent to those skilled in the art in view of applicants' disclosure of their presently preferred compositions and presently preferred methods. The foregoing detailed description has been given for clearness of understanding only, and no unnecessary limitations should be understood therefrom, as modifications therefrom will be apparent to those skilled in the art.

What is claimed is:

1. A primer/bonding-resin composition comprising:
   (A) a polymerizable resin component comprising a mixture of
   (i) at least one of a hydrophilic primer monomer having at least one carboxylic acid group and at least one polymerizable vinyl group, said primer monomer comprising a reaction product of at least one of an anhydride and a dianhydride compound with a compound having at least one vinyl group and at least one hydroxyl group,
   (ii) at least one high viscosity bonding resin compound having at least one reactive vinyl group, and
   (iii) a reactive monomer for diluting the viscosity of at least one of said high viscosity bonding resin compound and said hydrophilic primer monomer, said reactive monomer having at least one vinyl group reactive with at least one of said high viscosity bonding resin and said hydrophilic monomer;
   (B) a photo-initiator system for initiating polymerization of said resin component when said system is combined with said resin component and exposed to activating radiation; and
   (C) a solvent for dissolving or suspending said resin component and said photo-initiator system in a flowable form,
   wherein said resin component, said photo-initiator system and said solvent are selected so that a mixture thereof results in a shelf stable composition substantially polymerizable upon exposure of said mixture to at least one of an activating radiation and an external polymerization catalyst.

2. The composition of claim 1 wherein said polymerizable resin component is between about 2 wt. % and about 80 wt. % of said composition.

3. The composition of claim 1 wherein said hydrophilic primer monomer is between about 0.5 wt. % and about 50 wt. % of said composition.

4. The composition of claim 1 wherein said hydrophilic primer monomer is between about 2 wt. % and about 40 wt. % of said composition.

5. The composition of claim 1 wherein said hydrophilic primer monomer is between about 5 wt. % and about 30 wt. % of said composition.

6. The composition of claim 1 wherein said hydrophilic primer monomer is selected from the group consisting of BPDM, EDMT, DSDM, PMDM, PMGDM and mixtures thereof.

7. The composition of claim 6 wherein said hydrophilic primer monomer is selected from the group consisting of BPDM and EDMT and mixtures thereof.

8. The composition of claim 7 wherein said hydrophilic primer monomer is BPDM.

9. The composition of claim 1 wherein said hydrophilic primer monomer is a reaction product of at least one of an anhydride and a dianhydride with a compound having at least one reactive hydroxyl group and at least one vinyl group.

10. The composition of claim 1 wherein said high viscosity bonding resin compound is between about 0.5 wt. % and about 50 wt. % of said composition.

11. The composition of claim 1 wherein said high viscosity bonding resin compound is between about 1 wt. % and about 30 wt. % of said composition.

12. The composition of claim 1 wherein said high viscosity bonding resin compound is between about 5 wt. % and about 15 wt. % of said composition.

13. The composition of claim 1 wherein said high viscosity bonding resin compound is selected from the group consisting of Bis-GMA, DPEPA, PEDM, UDMA, and mixtures thereof.

14. The composition of claim 1 wherein said reactive monomer for diluting the viscosity of said high viscosity bonding resin compound is between about 0.5 wt. % and about 50 wt. % of said composition.

15. The composition of claim 1 wherein said reactive monomer for diluting the viscosity of said high viscosity bonding resin compound is between about 1 wt. % and about 30 wt. % of said composition.

16. The composition of claim 1 wherein said reactive monomer for diluting the viscosity of said high viscosity bonding resin compound is between about 5 wt. % and about 25 wt. % of said composition.

17. The composition of claim 1 wherein said reactive monomer for diluting the viscosity of said high viscosity bonding resin compound is selected from the group consisting of 2-HEMA, GM, HPMA, and mixtures thereof.

18. The composition of claim 1 wherein said photoinitiator system comprises a mixture of
 (A) a light-sensitive initiator compound; and
 (B) a polymerization accelerator compound activatable by said light-sensitive initiator compound to a state causing accelerated polymerization of said resin component, said accelerator compound selected from the group consisting of
  (i) a tertiary aromatic amine compound having the formula

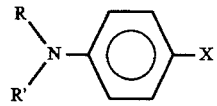

wherein R is at least one of $C_1$–$C_3$ alkyl, $C_1$–$C_3$ alkyl alcohol, and $CN(CH_2)_n$ wherein n is 1–3; R' is at least one of $C_1$–$C_3$ alkyl, $C_1$–$C_3$ alkyl alcohol, and $CN(CH_2)_n$ wherein n is 1–3; and X is an electron-withdrawing substituent; and
  (ii) a cyclic amine compound having the formula

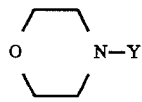

wherein Y is selected from the group consisting of $CH_2CH_2Z$, $CH_2CH_2CH_2Z$, and $CH_2CH(CH_3)Z$ wherein Z is selected from the group consisting of acrylates, methacrylates, alcohols, carboxylic acids, derivatives of carboxylic acids, halogens, and other substituents which do not prevent polymerization of said resin component.

19. The composition of claim 18 wherein R is selected from the group consisting of $CH_3$, $CH_2CH_3$, and $CH_2CH_2CH_3$ and R' is selected from the group consisting of $CH_3$, $CH_2CH_3$, and $CH_2CH_2CH_3$.

20. The composition of claim 18 wherein Y selected from the group consisting of ethyl methacrylate and isopropyl methacrylate.

21. The composition of claim 18 wherein X is selected from the group consisting of COOH, alkali metal salts of COOH, COOR" wherein R" is an alkyl group, $SO_3H$, salts of $SO_3H$, CHO, halogen atoms, $CH_2COOH$, salts of $CH_2COOH$, and CN.

22. The composition of claim 18 wherein said light-sensitive initiator compound is an alpha-diketone.

23. The composition of claim 18 wherein said light-sensitive initiator compound is selected from the group consisting of camphorquinone and derivatives thereof.

24. The composition of claim 18 wherein said light-sensitive initiator compound is between about 0.01 wt. % and about 5 wt. % of said composition.

25. The composition of claim 18 wherein said light-sensitive initiator compound is between about 0.05 wt. % and about 2 wt. % of said composition.

26. The composition of claim 18 wherein said light-sensitive initiator compound is between about 0.1 wt. % and about 1.0 wt. % of said composition.

27. The composition of claim 18 wherein said photoinitiator system comprises camphorquinone and said tertiary aromatic amine compound.

28. The composition of claim 18 wherein said polymerization accelerator compound comprises said tertiary aromatic amine compound being selected from the group consisting of DMABA, EDMAB and DMABAL.

29. The composition of claim 27 wherein said tertiary aromatic amine compound is selected from the group consisting of DMABA and DMABAL.

30. The composition of claim 29 wherein said tertiary aromatic amine compound is DMABAL.

31. The composition of claim 18 wherein said polymerization accelerator compound is between about 0.01 wt. % and about 10 wt. % of said composition.

32. The composition of claim 18 wherein said polymerization accelerator compound is between about 0.05 wt. % and about 5 wt. % of said composition.

33. The composition of claim 1 wherein said solvent is between about 5 wt. % and about 98 wt. % of said composition.

34. The composition of claim 1 wherein said solvent is between about 10 wt. % and about 90 wt. % of said composition.

35. The composition of claim 1 wherein said solvent is between about 20 wt. % and about 80 wt. % of said composition.

36. The composition of claim 1 wherein said solvent is selected from the group consisting of water, ethanol, acetone, and mixtures thereof.

37. The composition of claim 1 wherein said solvent comprises a mixture of ethanol, acetone and optionally water.

38. The composition of claim 37 wherein said solvent is a mixture of ethanol and acetone.

39. The composition of claim 36 wherein said solvent is ethanol.

40. The composition of claim 36 wherein said solvent is acetone.

* * * * *

UNITED STATES PATENT AND TRADEMARK OFFICE
CERTIFICATE OF CORRECTION

PATENT NO. : 5,658,963

DATED : August 19, 1997

INVENTOR(S) : Qian et al.

It is certified that error appears in the above-identified patent and that said Letters Patent is hereby corrected as shown below:

Column 1, line 32 delete "Ideal/y" and replace with —Ideally—.

Column 2, line 29, delete "alga" and replace with --alia--.

Column 3, line 36, insert --system-- between "two-component" and "was".

Column 4, line 22, delete "diglycidyimethacrylate" and replace with --diglycidylmethacrylate--.

Column 7, line 43, delete "mount" and replace with --amount--.

Column 7, line 54, delete "fight" and replace with --light--.

Column 9, line 53, delete "fight" and replace with --light--.

Column 9, line 63, insert --compositions-- after "primer/bonding-resin".

Column 10, line 18, delete "fried" and replace with --filled--.

Column 10, line 19, delete "fried" and replace with --filled--.

Column 10, line 44, delete "carded" and replace with --carried--.

Column 12, line 7, delete "Co)(2)" and replace with --(b)(2)--.

Column 13, line 29, delete "1α" and replace with --4--.

Column 13, line 44, delete "Co)(2)" and replace with --(b)(2)--.

Column 13, line 59, delete "Co)(2)" and replace with --(b)(2)--.

Column 14, line 15, delete "140(b)" and replace with --14(b)--.

UNITED STATES PATENT AND TRADEMARK OFFICE
CERTIFICATE OF CORRECTION

PATENT NO. : 5,658,963
DATED : August 19, 1997
INVENTOR(S) : Qian et al.

It is certified that error appears in the above-identified patent and that said Letters Patent is hereby corrected as shown below:

Column 14, line 34, delete "OO)(1)" and replace with --(b)(1)--.

Column 17, line 36, delete "(b)O)" and replace with --(b)(1)--.

Column 18, line 54, delete "mounts" and replace with --amounts--.

Column 22, claim 22, line 1, delete "fight" and replace with --light--.

Signed and Sealed this

Nineteenth Day of May, 1998

Attest:

BRUCE LEHMAN

Attesting Officer    Commissioner of Patents and Trademarks